United States Patent [19]

Adler

[11] Patent Number: 4,476,224

[45] Date of Patent: Oct. 9, 1984

[54] MATERIAL AND METHOD FOR PROMOTING THE GROWTH OF ANAEROBIC BACTERIA

[76] Inventor: Howard I. Adler, 128 Indian La., Oak Ridge, Tenn. 37830

[21] Appl. No.: 376,640

[22] Filed: May 10, 1982

[51] Int. Cl.$^3$ .............................................. C12N 1/20
[52] U.S. Cl. ................................. 435/253; 435/801; 435/820
[58] Field of Search .............. 435/253, 801, 189, 244, 435/253, 260, 262, 317, 820, 190, 191, 192; 426/8

[56] References Cited

PUBLICATIONS

Seiyaku, Abstract of Japanese Patent J56005-092, Jan. 1981.
*Fundamentals of Microbiology*, Frobisher, 7th Ed., Saunders Co., Philadelphia, 1962, pp. 422-423.
Adler, et al., "Cytoplasmic Membrane Fraction that Promotes Septation in an *Escherichia coli* Ion Mutant", *Journal of Bacteriology*, (Aug. 1981), pp. 326-332.
Adler et al., "A Novel Approach to the Growth of Anaerobic Microorganisms", *Biotechnology and Bioengineering Sump.*, No. 11, (1981), pp. 533-540.
*American Type Culture Collection Catalogue of Strains 1*, 15th Ed., Rockville, MD, American Type Culture Collection, 1982, pp. 115-116.
*American Type Culture Collection Catalogue of Strains 1*, 13th Ed., Rockville, MD, American Type Culture Collection, 1978, pp. 72-73.
Davis et al., *Microbiology*, Hagerstown, MD, Harper & Row, 1973, p. 187.
Anis et al., Some Enzymatic Activities of Particulare Fraction from Sonic Lysates of *Escherichia Coli*, J. of Bacteriology, vol. 72, pp. 314-319.

*Primary Examiner*—Robert J. Warden
*Assistant Examiner*—Randall E. Deck
*Attorney, Agent, or Firm*—Luedeka & Neely

[57] ABSTRACT

A material and method for promoting the growth of anaerobic bacteria which includes a nutrient media containing a hydrogen donor and sterile membrane fragments of bacteria having an electron transfer system which reduces oxygen to water. Dissolved oxygen in the medium is removed by adding the sterile membrane fragments to the nutrient medium and holding the medium at a temperature of about 10° to about 60° C. until the dissolved oxygen is removed.

10 Claims, No Drawings

MATERIAL AND METHOD FOR PROMOTING THE GROWTH OF ANAEROBIC BACTERIA

The U.S. Government has rights in this invention pursuant to Contract No. W-7405-ENG-26 awarded by the Department of Energy.

The present invention relates generally to promoting the growth of anaerobic bacteria and in particular relates to the use of sterilized bacterial derivatives for the obtainment of anaerobic conditions in media to promote the growth of anaerobes.

Many of the bacteria present in natural environments are sensitive to oxygen and will not grow in its presence. When these organisms (known as anaerobes) are brought into the laboratory, it is often necessary to employ cumbersome physical and chemical techniques in order to get them to grow. Some of these bacteria produce diseases of man and related species. Other produce important industrial end products such as methane, hydrogen and various alcohols. The manipulation of these organisms is, to some degree, limited by the ease with which they can be grown.

As pointed out above, in order to grow anaerobes it is necessary that the media in which the anaerobe is to be grown is substantially free of oxygen. Oxygen can be removed fairly efficiently from a liquid media by sparging it with high purity nitrogen or other inert gas. However, the liquid media which are employed are subject to foaming so that this process presents a number of mechanical difficulties. Further, after sparging is stopped, the medium is easily recontaminated with oxygen.

Oxygen can also be removed from liquid media by the addition of reducing agents. However, most of these agents are strong reducing agents and any residual agent or its by-products in the media tends to inhibit the subsequent growth of anaerobes in the media. Also, the reducing agent which is consumed during the initial removal of oxygen is not available to act upon oxygen which might later find its way into the system.

In the case of a solid medium, such as agar, oxygen removal with an inert gas is difficult to accomplish because the oxygen in the medium comes to equilibrium with the inert atmosphere slowly and never reaches a zero concentration. Reducing agents can be added to a solid media but again there is still the problem of the inhibition of anaerobic growth in the media due to any residual reducing agent or its by-products as well as the problem of providing the system with the ability to consume any oxygen which might later find its way into the system.

The principal object of the invention is to provide an improved material and means to effect the removal of dissolved oxygen from media in which anaerobic bacteria are to be grown. A more specific object of the invention is the provision of sterile membrane fragments of oxygen-consuming bacteria and a method of using such membrane fragments in connection with the growth of anaerobic bacteria. Other objects and advantages of the invention will become known from the following description of various embodiments and examples of the invention.

I have discovered that sterilized membrane fragments from certain oxygen-consuming bacteria may be incorporated into media, either liquid or solid, to remove oxygen rapidly and completely from the media. As will be pointed out, in some instances it is necessary to incorporate in the media a small amount of a suitable hydrogen donor so that reduction of the oxygen to water is facilitated. It has been found that the sterile membrane fragments can be employed without foaming problems and that the presence of the membranes has no adverse effect upon the growth of the anaerobic bacteria in the media. No toxicity has been observed in a large number of anaerobes which have been grown in media which has been treated with the sterilized membrane fragments to remove oxygen, even in the presence of a ten-fold excess of membrane fragments. Further the presence of the membrane fragments in the media provides the media with the capacity to reduce additional oxygen which later may enter the system so that extreme methods of sealing the system are not required.

A great number of bacteria have membranes which contain an electron transport system that effectively reduces oxygen to water if a suitable hydrogen donor is present in the medium. Some of the sources of oxygen-reducing membranes are *Escherichia coli, Salmonella typhimurium, Gluconobacter oxydans,* and *Pseudomonas aeruginosa.* Preferred results are obtained with *E. coli* B/ORNL (also identified as ATCC E11303), *E. coli* B/r ORNL (also identified as ATCC 12407) and *E. coli* K12. Cultures grown in complex media such as supplemented nutrient broth or Luria broth have a higher specific activity than cultures grown in synthetic media although the activity of synthetic-grown cells can be increased if glycerol or acetate is substituted for glucose.

The process of producing the useful membrane fragments involves the following steps:

1. Bacteria having membranes containing an electron transfer system which reduces oxygen to water are grown under suitable conditions of active aeration and a temperature which is conducive to the growth of the bacteria, usually about 37° C. in a broth media.

2. The bacterial cells are harvested by centrifugation or filtration, and are washed with distilled water.

3. A concentrated suspension of the cells is treated to break up the cells into fine particles. This is accomplished by known means, for example, by ultra sonic treatment or by passing the suspension several times through a French pressure cell at 20,000 p.s.i., or the like.

4. The cellular debris is removed. This may be accomplished by centrifugation at 12,000×g for about 15 minutes at 5° C.

5. The suspended membrane fragments are separated from the supernatant liquid from step 4. This is accomplished, for example, by centrifugation at 175,000×g at 5° C.

6. The recovered membrane fragments are resuspended in a buffer solution at a pH of about 7.0 to about 7.5. A preferred buffer solution is a 0.02 molar solution of N-2-hydroxyethylpiperazine-$N^1$-2-ethane sulfonic acid (HEPES).

7. The membrane fragments in the buffer solution are then passed under pressure through a filter having openings of a size which will retain any intact microorganisms to effect sterilization. Openings of about 0.2 microns are satisfactory.

8. The sterilized suspension is then preferably used promptly or stored for use at about −20° C. or it may be freezedried.

In use, a small amount of the sterile membrane fragment suspension is added to a liquid medium which is to be used for the growth of the anaerobic bacteria (about 25 to 3000 mg of fragments per liter of medium). The medium is permitted to stand for a short period of time at a temperature of from about 10° to about 60° C. until the oxygen is consumed. This action takes up to about 20 to 30 minutes, depending upon the concentration of the sterile membrane fragments and the temperature. At concentrations of about 500 mg/l and temperatures of about 35° C., removal is effected in from about 2-8 minutes. After the oxygen is removed, an inoculum of anaerobic bacteria is introduced into the medium. The inoculated medium is then incubated for the growth period at the proper temperature for the bacteria which are to be grown. Preferably, the air space above the liquid medium in its container is flooded with an inert gas such as nitrogen. This minimizes the amount of oxygen that must be removed by the membrane system and prolongs the life of the oxygen-consuming system. This also gives assurance that if there is an accidental leak of air into the system that the system will consume that air and insure that the growth of the anaerobic bacteria will not be retarded.

In the case of a solid medium, such as agar, the membrane preparation is preferably added to medium in a molten state at approximately 45° C. at a level of about 25 to 3000 mg of fragments per liter of medium. The medium is then poured into Petri dishes, or the like, in which it is held at a temperature of from about 10° to about 60° C. until the oxygen is consumed, usually in a period of time less than 20 to 30 minutes. The time of removal depends upon the temperature and concentration of the sterile membrane fragments, as pointed out above. The medium is then inoculated with the anaerobe to be grown and incubated at the proper temperature for growth. Again, the Petri dishes should preferably be maintained in an atmosphere of inert gas, such as nitrogen, but good results have been obtained on rapidly growing anaerobes without such a precaution since the membrane system is capable of consuming reasonable amounts of oxygen from any air which may leak into the dish.

In the event that a synthetic media is employed it may be necessary to add a small amount of a hydrogen donor which does not interfere with the growth of the selected anaerobic bacteria. Suitable hydrogen donors are sodium lactate, sodium succinate, α glycerol phosphate, or sodium formate. Most natural media do not require the addition of a hydrogen donor but with some media, particularly synthetic media, the addition of the hydrogen donor is necessary for the sterile membrane fragments to perform their oxygen removing function.

Tests have shown that some 18 species of anaerobic bacteria representing 8 different genera have flourished in media which has had its oxygen removed by the sterile membrane system. It has been found that because of the fact that the sterile membrane fragments are in the form of particles which do not penetrate the cell walls that the system does not adversely affect the anaerobes being grown. This is in contrast to a system in which a chemical-reducing agent is used to accomplish the removal of dissolved oxygen when the residual reducing agent or its by-product may penetrate the cell walls. Thus, because the anaerobic bacteria are being grown under more natural conditions they flourish at a greater rate than in media which has been treated with such reducing agents.

EXAMPLE I

A nutrient broth is inoculated with *E. coli* B/r ORNL. The nutrient broth employed was a nutrient broth sold under the trade name Difco Nutrient Broth manufactured by Difco Laboratories, Detroit, Mich. This broth is a beef extract which includes digested peptides. The nutrient broth was supplemented with a high purity yeast extract in an amount of 0.1 percent by weight and with sodium chloride at a level of 0.6 percent by weight. The high purity yeast extract which was employed was manufactured by Difco Laboratories, Detroit, Mich., and sold under the trade name Difco Yeast Extract. The inoculated broth was maintained at about 37° C., and was actively aerated. The growth was continued until it was in the late logarithmic phase.

The broth containing the *E. coli* was centrifuged at $4,000 \times g$ to harvest the bacterial cells. The cells were washed with distilled water and centrifuged. This washing and centrifuging was repeated.

The harvested cells were suspended in distilled water at a concentration of about 0.4 g/ml and were then ruptured and broken up. This was accomplished by passing the suspensions three times through a French pressure cell operated at 20,000 psi. The suspension with the broken-up cells was then centrifuged at $12,000 \times g$ for 15 minutes at 5° C. to remove undesired cellular debris.

The supernatant liquid, from which the large cellular debris had been removed, was centrifuged for about 4½ hours at $175,000 \times g$ at 5° C. to obtain membrane fragments.

The membrane fragments were then resuspended in a 0.02 molar HEPES buffer solution (manufactured by the Calbiochem-Behring Corp. of LaJolla, Ca.). The buffer had a pH of 7.5.

The suspension of the membrane fragments in the buffer solution was then passed through a 0.22 micron filter under pressure to produce the sterile membrane fragments to be used to produce anaerobosis in the media to be used for growing anaerobes. The suspension of membrane fragments was stored at about −20° C. The dry weight of the solids in the suspension was about 30 mg/ml which was determined by dessicating samples over phosphorous pentoxide in a vacuum.

EXAMPLE II

Ten microliters of the suspension of sterilized membrane fragments from Example I was added per milliliter of oxygen saturated Difco Nutrient Broth at 37° C. Tests showed that in five minutes all of the oxygen was removed. A portion of the nutrient broth which had been treated with the sterilized membrane fragments and which had been held until anaerobic conditions were obtained was inoculated with *Clostridium difficile* and incubated at 37° C. for 16 hours in a sealed container. A luxuriant growth of approximately $10^9$ cells/ml was observed.

EXAMPLE III

Ten microliters of the sterile membrane fragment preparation of Example I is added per milliliter of synthetic medium which was supplemented by the addition of sodium lactate to a final concentration of 0.25M. The synthetic medium consists generally of inorganic salts, ethanol and sodium acetate. It is prepared from reagent grade chemicals. A sample of medium containing the membrane fragments was held at 37° C. to remove oxygen and was inoculated with *Clostridium kluyveri*. The inoculated medium was incubated at 34° C. for 96 hours. At the end of that time a luxuriant growth of approximately $10_9$cell/ml was observed.

EXAMPLE IV

The sterile membrane fragment suspension of Example I was added to molten agar at 45° C. at a level of 10 microliters of suspension per milliliter of agar. The agar was poured into a Petri dish and held to obtain anaerobic conditions. It was inoculated with *Clostridium kluyveri* and incubated in the presence of an inert gas atmosphere at a temperature of 34° C. for a period of 96 hours. Colonies with a diameter of approximately 2 millimeters were observed at that time.

Tests have shown that similar results are observed with sterilized membrane fragments from *E. coli* B/ORNL, *E. coli* K-12, *Salmonella typhimurium*, *Gluconobacter oxydans* and *Pseudomonas aeruginosa*. In all cases the concentration of membrane fragments in the sterile membrane suspension was about 25-30 mg/ml. At 37° C. all of the oxygen is removed from the the nutrient media in from about 2 to about 8 minutes when the membrane fragment suspension is present at from about 10 to about 100 milliliters per liter of broth (250-3000 mg of fragments per liter of broth). At higher levels, oxygen removal is more rapid than at lower levels.

As pointed out above, when a synthetic media or one not containing a hydrogen donor is employed, a hydrogen donor which is compatible with the bacteria being cultured should be employed to supplement the medium. The hydrogen donor, e.g. sodium lactate, sodium succinate, α glycerol phosphate, or sodium formate should be employed at a level of the order of 0.15 to 0.25M.

Anaerobic bacteria which have been successfully grown in nutrient media treated by the sterile membrane system described herein are:
*Clostridium difficile*
*Clostridium tetani*
*Clostridium kluyveri*
*Clostridium sporogenes*
*Clostridium perfringens*
*Clostridium sordelli*
*Clostridium butyricum*
*Clostridium bifermentans*
*Clostridium acetobutyricum*
*Peptostreptococcus anaerobius*
*Peptostreptococcus micros*
*Peptostreptococcus magnus*
*Desulfovibrio vulgaris*
*Fusobacterium nucleatum*
*Viellonella parvula*
*Propionibacterium acnes*
*Eubacterium limosum*
*Bacteroides fragilis*

The use of sterile membrane-containing media may be used in clinical laboratories to stimulate growth of anaerobic bacteria from human patients. Sterile membrane containing media may be used to increase the survival of anaerobes in medium used to transport samples from the patient to the laboratory and also for the determination of antibiotic sensitivity patterns of anaerobic bacteria. It also has use in producing the anaerobic conditions required in many industrial fermentation processes. The use of sterile membrane fragments, as described above, produce little or no toxic side effects when used in amounts much greater than those required to achieve oxygen-free conditions. Small quantities of the membrane fragments reduce a medium that is initially saturated with oxygen to an anaerobic condition and maintain that condition even though small amounts of air are introduced.

Various features of the invention are set forth in the appended claims.

What is claimed is:

1. A nutrient medium for growing anaerobic bacteria which includes a hydrogen donor and sterile membrane fragments derived from bacteria having membranes containing an electron transfer system which reduces oxygen to water.

2. The nutrient medium of claim 1 in which the sterile membrane fragments are present in a concentration of from about 25 to 3000 mg/l.

3. A nutrient medium for growing anaerobic bacteria which includes a hydrogen donor and sterile membrane fragments derived from bacteria selected from the class consisting of *Escherichia coli*, *Salmonella typhimurium*, *Gluconobacter oxydans*, and *Psuedomonas aeruginosa*.

4. The nutrient medium of claim 3 wherein the sterile membrane fragments are derived from bacteria selected from the class consisting of *E. coli* B/ORNL, *E. coli* B/r ORNL, and *E. coli* K12.

5. The nutrient medium of claim 1 wherein the hydrogen donor is selected from the group consisting of sodium lactate, sodium succinate, sodium formate and α glycerol phosphate.

6. The method of removing dissolved oxygen from a nutrient medium for anaerobic bacteria comprising the steps of introducing sterile membrane fragments derived from bacteria having membranes which contain an electron transfer system which reduces oxygen to water in the presence of a hydrogen donor to the nutrient medium and maintaining the medium containing sterile membrane fragments at a temperature of from about 10° to about 60° C. until the dissolved oxygen is converted to water.

7. The method of claim 6 further comprising the step of adding a hydrogen donor to the nutrient medium.

8. The method of claim 7 wherein the hydrogen donor is selected from the group consisting of sodium lactate, sodium succinate, sodium formate and α glycerol phosphate.

9. A method of removing dissolved oxygen from a nutrient medium for anaerobic bacteria comprising the steps of introducing sterile membrane fragments derived from bacteria selected from the class consisting of *Escherichia coli*, *Salmonella typhimurium*, *Gluconobacter oxydans*, and *Pseudomonas aeruginosa* to the medium and maintaining the medium containing sterile membrane fragments at a temperature of from about 10° C. to about 60° C. until the dissolved oxygen is converted to water.

10. The method of claim 9 wherein the sterile membrane fragments are derived from bacteria selected from the class consisting of *E. coli* B/ORNL, *E. coli* B/r ORNL, and *E. coli* K12.

* * * * *